(12) United States Patent
Xia et al.

(10) Patent No.: US 8,547,553 B2
(45) Date of Patent: Oct. 1, 2013

(54) FIBER OPTIC HYDROGEN PURITY SENSOR AND SYSTEM

(75) Inventors: Hua Xia, Altamont, NY (US); Shashank Nath Khandavalli, Alpharetta, GA (US)

(73) Assignee: General Electric Company, Niskayuna, NY (US)

( * ) Notice: Subject to any disclaimer, the term of this patent is extended or adjusted under 35 U.S.C. 154(b) by 124 days.

(21) Appl. No.: 12/725,664

(22) Filed: Mar. 17, 2010

(65) Prior Publication Data

US 2011/0228275 A1   Sep. 22, 2011

(51) Int. Cl.
*G01N 21/00*   (2006.01)

(52) U.S. Cl.
USPC ............................. 356/437; 356/444

(58) Field of Classification Search
USPC ................... 356/237.1–237.5, 437
See application file for complete search history.

(56) References Cited

U.S. PATENT DOCUMENTS

| | | | |
|---|---|---|---|
| 4,531,070 A | 7/1985 | Kuhn | |
| 5,088,315 A | 2/1992 | Johnson | |
| 5,186,277 A | 2/1993 | Snuttjer et al. | |
| 5,785,114 A | 7/1998 | Armstrong et al. | |
| 5,956,970 A | 9/1999 | Sato et al. | |
| 6,126,726 A | 10/2000 | Foley, Jr. et al. | |
| 6,535,658 B1 * | 3/2003 | Mendoza et al. | 385/12 |
| 7,151,872 B1 | 12/2006 | Xia et al. | |
| 7,228,017 B2 | 6/2007 | Xia et al. | |
| 7,340,119 B1 | 3/2008 | Xu et al. | |
| 7,421,162 B2 * | 9/2008 | McCarthy et al. | 385/37 |
| 7,448,252 B2 | 11/2008 | Brosnihan et al. | |
| 7,469,077 B2 | 12/2008 | Xia et al. | |
| 7,489,835 B1 | 2/2009 | Xia et al. | |
| 7,552,622 B2 | 6/2009 | Speranza | |
| 7,574,075 B2 | 8/2009 | Xia | |
| 7,887,910 B2 * | 2/2011 | Kuramoto et al. | 428/323 |
| 2004/0173004 A1 | 9/2004 | Eblen et al. | |
| 2005/0186117 A1 * | 8/2005 | Uchiyama et al. | 422/91 |
| 2008/0291456 A1 * | 11/2008 | Ghislain | 356/450 |
| 2009/0046379 A1 * | 2/2009 | Kuramoto et al. | 359/718 |

FOREIGN PATENT DOCUMENTS

WO   2008136870 A2   11/2008

OTHER PUBLICATIONS

Search Report from corresponding GB Application No. GB1103985.6 mailed Jul. 5, 2011.

* cited by examiner

*Primary Examiner* — Tarifur Chowdhury
*Assistant Examiner* — Isiaka Akanbi
(74) *Attorney, Agent, or Firm* — Nitin Joshi (57) ABSTRACT

A hydrogen purity sensing system includes a light source which provides an optical signal through a fiber optic cable. A hydrogen purity sensor is provided in the system which comprises a multilayered nanostructural film of high refractive index and low refractive index materials for receiving the optical signal. The system further includes a photodetector for receiving a reflected optical signal from the hydrogen purity sensor and a processing circuitry coupled to the photodetector for analyzing the reflected optical signal.

23 Claims, 9 Drawing Sheets

FIBER OPTIC HYDROGEN PURITY SENSOR AND SYSTEM

BACKGROUND

The invention relates generally to hydrogen purity detection and fiber optical hydrogen purity sensors.

The global demand for hydrogen is increasing significantly because of its wide range of applications covering many industries such as fuel cells, transportation, and power generation. The purity requirement of hydrogen varies with the application. For example, a proton electrolate membrane fuel cell (PEMFC) requires high hydrogen purity to prevent catalyst poisoning.

Existing hydrogen purity monitoring instruments are typically based on thermal conductivity detection (TCD). TCD is a general-purpose gas analysis method with non-specific and nondestructive characteristics and is less sensitive than flame ionization detection methods. The resolution and accuracy of TCD is limited. Other methods for monitoring hydrogen purity include the use of gas density and differential pressure based measurements. However, these methods are subject to ambient and gas temperature-induced variations.

Therefore, there is a need for an improved hydrogen purity measurement sensor and system to address one or more aforementioned issues.

BRIEF DESCRIPTION

In accordance with an embodiment of the present invention, a hydrogen purity sensing system is provided. The system includes a light source which provides an optical signal through a fiber optic cable. A hydrogen purity sensor comprising a multilayered nanostructural film including high- and low-refractive index materials is provided in the system to receive the optical signal. The system further includes a photodetector for receiving a reflected optical signal from the hydrogen purity sensor and processing circuitry coupled to the photodetector for analyzing the reflected optical signal.

In accordance with another embodiment of the present invention, a hydrogen purity sensor including a fiber core and a refractive index periodic modulated grating structure positioned about the core is provided. The sensor further includes a fiber cladding surrounding the refractive index periodic modulated grating structures and a multilayered sensing film positioned about the fiber cladding. The sensing film includes a modulated structure of multiple high refractive index and low refractive index material layers.

In accordance with yet another embodiment of the present invention, a hydrogen purity sensor package is provided. The sensor package includes a multilayered nanostructural film of hydridable and non-hydridable materials and at least two fiber Bragg gratings installed in a thermally insensitive quartz material-based chamber.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Figure 1:
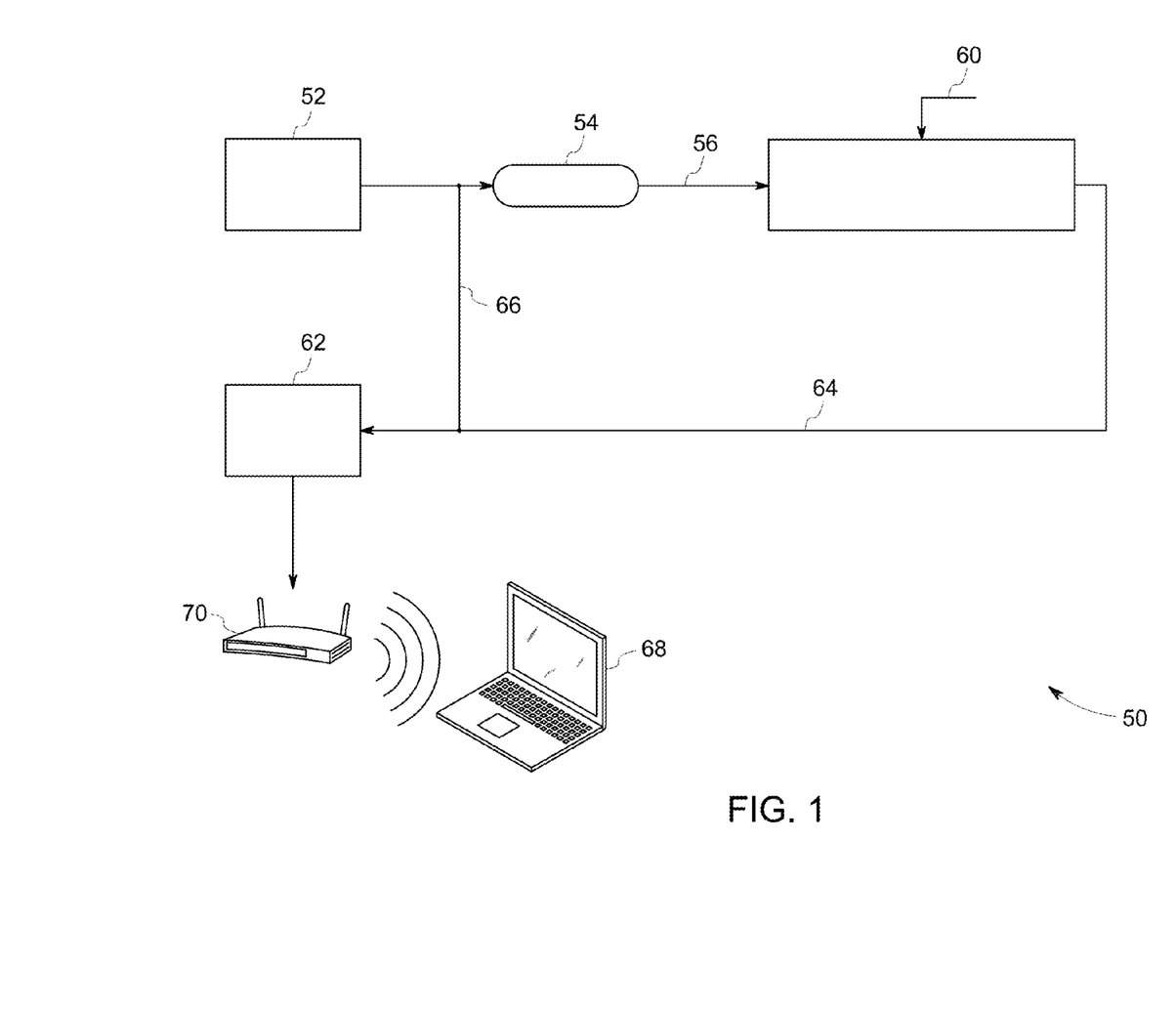
FIG. 1 is a schematic view of a hydrogen purity sensing system including a fiber gas hydrogen purity sensor (FGHPS) package in accordance with an embodiment of the present invention.

FIG. 1 is a schematic illustration of a hydrogen purity sensing system 50 according to an embodiment of the invention. In general, the sensing system 50 includes a light source 52, such as tunable, broadband light source, in light communication with an optical coupler or circulator 54. The optical coupler 54 receives the light transmitted from the light source 52 and transmits a portion of the light through an optical fiber cable 56. The light passing through the optical fiber cable 56 enters one or more fiber gas hydrogen purity sensors 60. In one embodiment, a fiber gas hydrogen purity sensor package is installed inside an apparatus for hydrogen purity detection. In another embodiment, a plurality of fiber gas hydrogen purity sensors are installed at multiple locations for simultaneous multi-point hydrogen purity detection. A photodetector 62 positioned downstream of the fiber gas hydrogen purity sensors 60 receives the transmitted light from the gas sensors 60 through an optical fiber cable 64. A portion of the light reflected by the optical coupler 54 is also received by the photodetector 62 through an optical fiber cable 66. The converted light signal generated by fiber gas hydrogen purity sensor 60 is transmitted to a computer 68. In one embodiment, a wireless interface 70 transmits electrical signals to the computer 68, and the computer 68 uses the transmitted signals to monitor the purity of the hydrogen gas. In another embodiment, an Ethernet cable is used to transmit electrical signals to the computer 68, and the computer 68 uses the transmitted signals to analyze the hydrogen purity from a sampling source or targeted environment.

Figure 2:
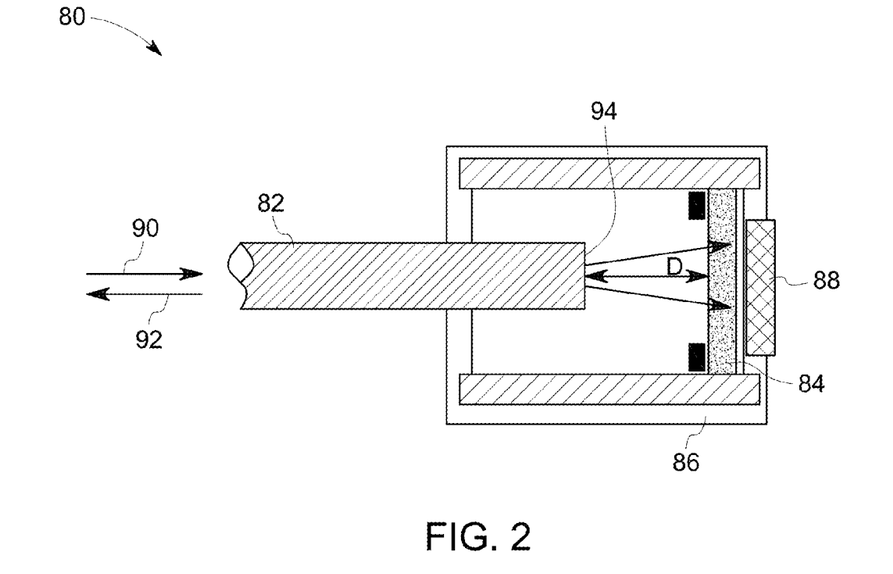
FIG. 2 is a schematic representation of an intensity-based fiber gas hydrogen purity sensor in accordance with an embodiment of the present invention.

FIG. 2 shows an intensity-based fiber gas hydrogen purity sensor 80 in accordance with an embodiment of the present invention. The sensor 80 comprises multi-furcated fiber reflectance probes as a combined fiber bundle 82 integrated with a nano-structural multilayered sensing chip 84. In one embodiment, the sensing chip 84 is installed in a sensing probe tip house or a chamber 86 which is thermally insensitive. At one end of the sensing probe tip house 86, the fiber bundle 82 is fixed, and at the second end of the sensing probe tip house 86, a filter 88 is fixed to allow filtered hydrogen gas inside the house 86 to interact with sensing chip. In this embodiment, the sensing chip faces the fiber bundle tip 94 and is adjacent filter 88.

Figure 3:
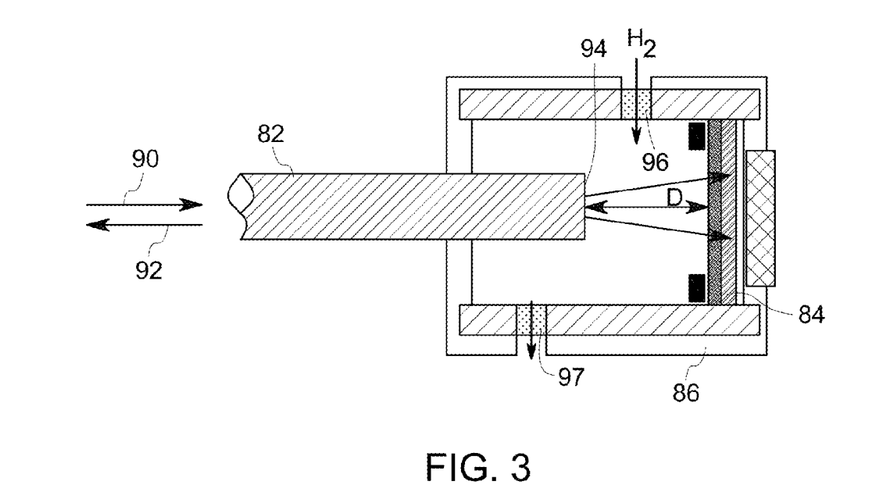
FIG. 3 is a schematic representation of another intensity-based fiber gas hydrogen purity sensor in accordance with an embodiment of the present invention.

FIG. 3 shows another intensity-based fiber gas hydrogen purity sensor 95 in accordance with an embodiment of the present invention. In this embodiment, two holes 96 and 97 with filters have been used to let H2 gas diffuse into the house 86 from one hole 96 and leave the house 86 from another hole 97. Filters of FIG. 2 and FIG. 3 may comprise a material such as Polytetrafluoroethylene (PTFE) as a membrane to block contaminants, oil-mists, and/or dust, for example. In one embodiment, the porous size of the membrane material ranges from 0.1 microns to 2 microns. In operation, a light signal 90 is incident onto the sensing chip, and the reflected signal 92 from the chip is measured. The reflected signal amplitude depends on the surface properties of the sensing chip which change according to the hydrogen purity. The hydride formation in the nanostructural multilayered sensing chip turns a surface which is opaque and mirror-like when no hydrogen is present into a more translucent surface in the presence of hydrogen, and thus, the surface reflectance or absorption can be used to determine hydrogen concentration or hydrogen purity. In one embodiment, the light signal or transmission signal may be from a laser source and the reflected signal or the reflection light may be detected by a Si-based photodiode or photodiode array.

In one embodiment of the present invention, a fiber bundle of seven fibers with central fiber for emitting light and six fibers to pick up reflectance from target surface is utilized. The fiber bundle probe may be of length 4-8 inches and of diameter 0.25-0.5 inches, for example. The reflected signal amplitude depends on the distance D between the fiber bundle tip or the probe tip 94 and the sensing chip 84.

Figure 4:
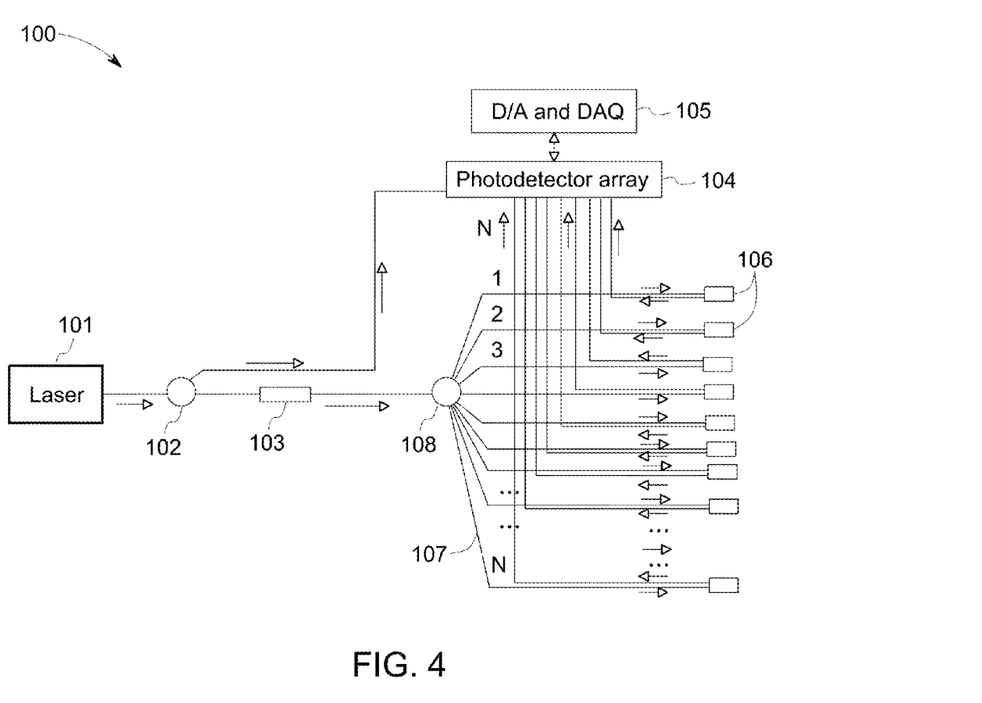
FIG. 4 is a schematic representation of a multiplexing scheme with intensity-based fiber gas hydrogen purity sensors in accordance with an embodiment of the present invention.

FIG. 4 illustrates a multiplexing scheme 100 used for multiple hydrogen purity sensors in accordance with an embodiment of the present invention. The scheme 100 includes a laser source 101, a first optical splitter 102, an optical coupler 103, and a photodetector array 104. The scheme further includes multiple hydrogen sensor housings 106 similar to FIG. 2 or FIG. 3 and a processing circuitry 105 having a digital to analog converter and a data acquisition module. In one embodiment, for a single fiber sensing probe, a direct light coupling from the laser source 101 to a fiber bundle can be realized by using FC/UPC or SMA 905 connectors. One light source can be split into multiple sub-light-sources for illuminating multiple fiber sensing probes 107 using a second optical splitter 108. The first optical splitter 102 splits the light signal from the laser source into two signals with one signal as a reference signal to the photodetector array 104 and another signal to the second optical splitter 108 through the optical coupler 103. In one embodiment, the split ratio of two light beams ranges from 1/99 to 5/95. The second optical splitter 108 is of length 1×N, where N is number of sensor housings. The second optical splitter equally splits the light signal into N split light signals, and each split light is sent to each fiber sensing probe and the reflected signal is then sent back to the photodetector array 104. The intensity-based reflected analog signals are converted into digital signals with a reference signal from the first optical splitter for suppressing drifting and light source degradation.

Figure 5:
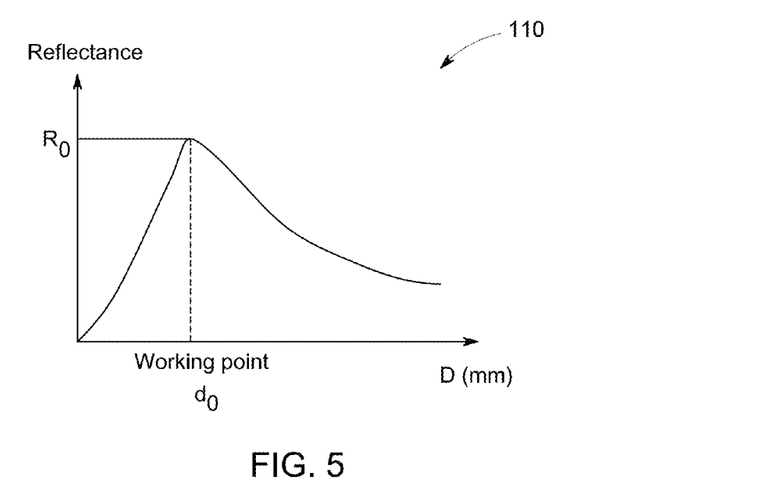
FIG. 5 is a plot of variation of reflected signal amplitude versus standoff distance of the fiber sensing probe from the sensing chip.

FIG. 5 shows a plot 110 of variation of reflected signal amplitude with respect to the distance D (shown in FIGS. 2, 3) between the probe tip and the sensing chip. For gas sensing in a vibrational environment, the standoff point of the fiber bundle tip from the sensing chip should be at a displacement insensitive position. A maximum reflected signal amplitude $R_0$ occurs at a standoff distance $d_0$. It can be seen from the plot that the signal amplitude can be changed by choosing a different standoff distance. At the maximum signal amplitude, the signal has no sensitivity to small distance variation, and any signal change can be attributed to sensing material reflectivity or absorption change.

Figure 6:
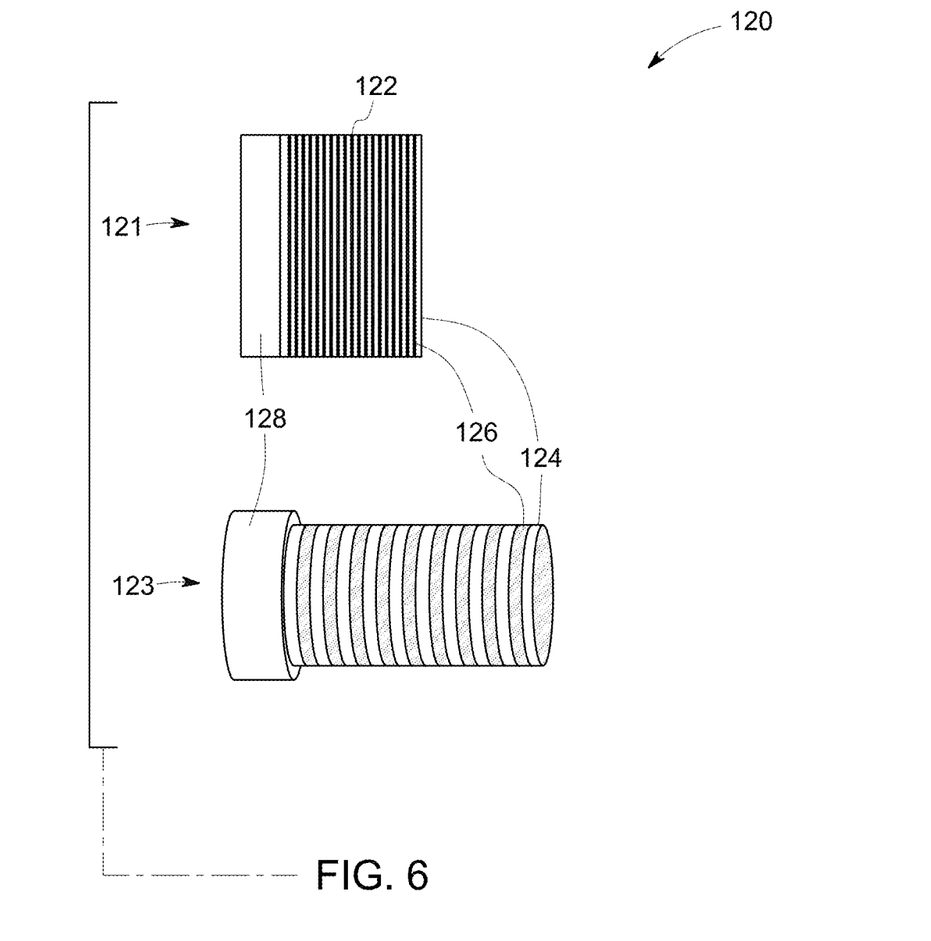
FIG. 6 is a schematic illustration of a multilayered sensing chip in accordance with an embodiment of the present invention.

FIG. 6 illustrates a hydrogen purity multilayered sensing chip 120 in accordance with an embodiment of the present invention. A two dimensional view of the sensing chip is shown by a referral numeral 121 and a three-dimensional view is shown by referral numeral 123. The chip 120 comprises a multilayered sensing film 122 of a high refractive index material 124 and a low refractive index material 126. The high refractive index material refers to a material which has higher refractive index compared to the refractive index of the fiber cladding of the optical fiber cable. Similarly low refractive index material refers to a material which has lower refractive index compared to the refractive index of fiber cladding of the optical fiber cable. In one embodiment, the refractive index of fiber cladding is about 1.45, hence the refractive index of the high refractive index material may be 2 and of the low refractive index material may be 0.8. In another embodiment, the high refractive index material comprises a hydridable material such as palladium and its alloy material and low refractive index material comprises a non-hydridable material such as noble metals, supported by a substrate which in one embodiment comprises a quartz glass plate 128. It will be appreciated by those skilled in the art that hydridable material interacts with hydrogen atoms when the hydrogen atoms are available whereas non-hydridable material does not interact with hydrogen atoms. In one embodiment, the hydridable layer may be of a thickness ranging from 1-5 nanometers, and the non-hydridable layer may be of a thickness ranging from 1-3 nanometers. A bilayer is constructed by combining a hydridable layer and a non-hydridable layer as a fundamental building block. The film 122 may be fabricated by repeating such building blocks layer-by-layer using a computer controlled film deposition process.

In one embodiment, the hydridable material comprises a Palladium, or Palladium alloy (Pd(x) M(1−x), wherein M=Ag, Au, Cu, Ni), or palladium oxides (PdOx), and the non-hydridable material comprises noble metals such as gold (Au), silver (Ag), copper (Cu), or Nickel (Ni), which are used to increase solubility of the hydrogen atoms, thereby avoiding electrical conductivity saturation and increasing detectability of hydrogen gas on one hand and further increasing refractive index modulation in the multilayered sensing material on the other hand.

Figure 7:
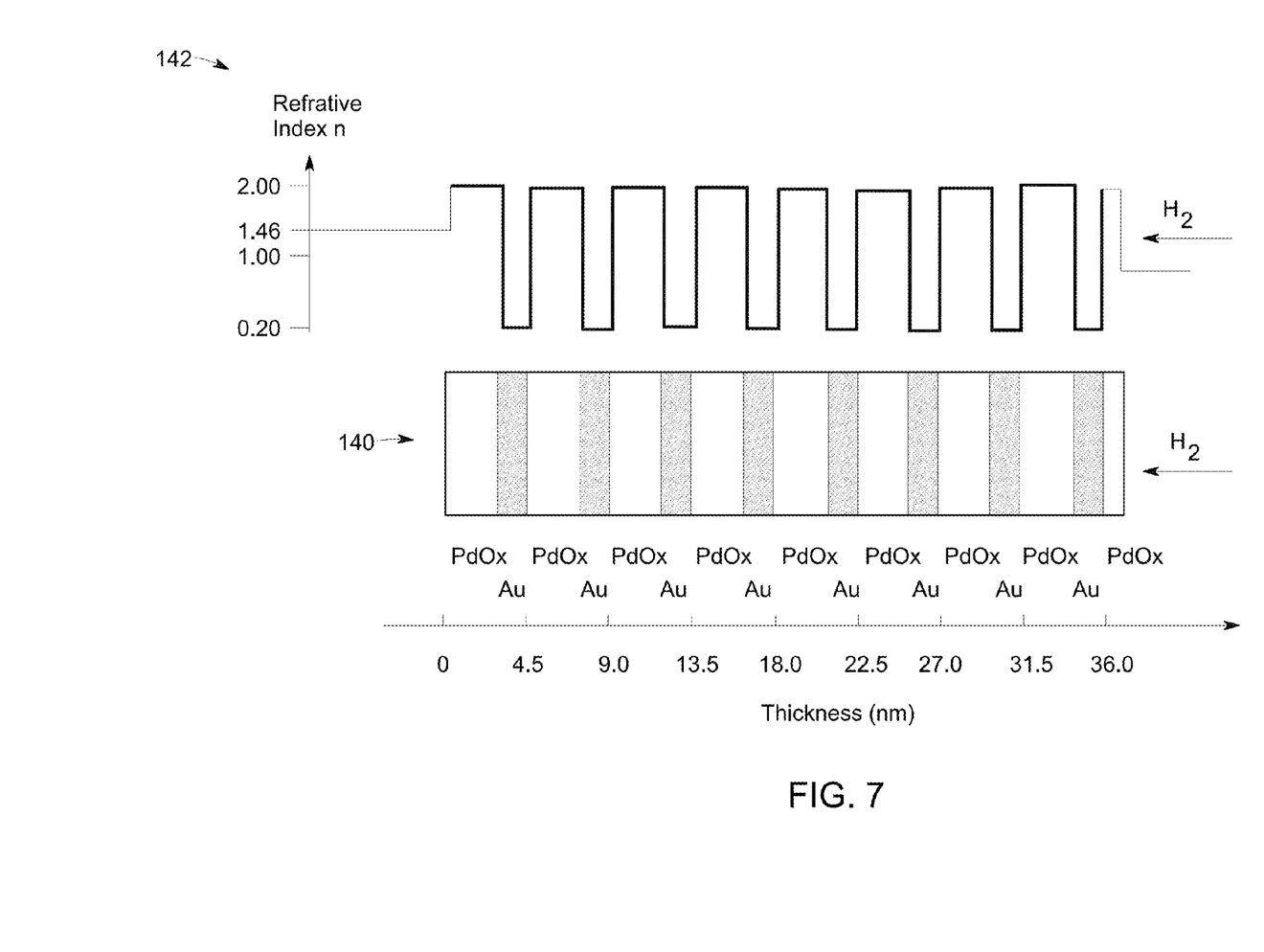
FIG. 7 is a schematic example of a high- and low-refractive index modulated sensing film with PdOx and Au as basic blocks.

FIG. 7 shows one example of a high and low refractive index multilayered sensing film 140 along with a refractive index plot 142. In this embodiment, the multilayered sensing film comprises PdOx and Au sublayers as high and low refractive index materials respectively. The PdOx/Au periodic modulated sensing film is prepared either in an Ar+O2 deposition condition, where O2 concentration ranges from 10-20%, or in an Ar deposition condition which follows a post-thermal-treatment process at O2-rich environment. Each layer has a specific thickness as shown on horizontal axis and refractive index as shown on vertical axis. By using different thicknesses, the coherent multilayered sensing structure allows the refractive index profile to be modulated resulting in significant optical property variation for light transmission, absorption, or reflection.

When the multilayered sensing film 140 interacts with hydrogen molecules, the first Pd top layer (shown as having a 1 nm thickness in FIG. 8) dissolves hydrogen molecules into hydrogen atoms. The diffusion of the H atoms backward-crosses nanoparticle boundaries in the single layer and crosses all nanoparticle boundaries and interface borders in the remaining layers. Pd nanoparticles are bonded to H atoms to form hydrides while partial Pd—O bonds become H—Pd—O—H in the hydridable PdOx layer, and partial H—Pd—O—H bonding clusters split into H—Pd and —OH hydroxyl ions The non-hydridable layers of Au in the multilayered sensing film provide interfacial boundaries and act as H atom diffusion channels. The high contrast in real refractive index between Pd (n~2.0) and Au (~0.2) effectively modulates the light propagating properties and the imaginary part of the refractive indices of two metal materials affects only the absorption properties. It will be appreciated by those skilled in the art that refractive index refers to ratio of light wavelength in vacuum with light wavelength in a medium for which refractive index is to be measured. The effective refractive index along the normal axis of the multilayered sensing film n(z) can be given as:

$$n(z) = \left[\frac{d(PdOx)}{d}*n(Pd) + \frac{d(Au)}{d}*n(Au)\right] + \sum_i A_i * e^{-i*k*z} \quad (1)$$

where d=d(PdOx)+d(Au) and is defined as the modulation length of the multilayered sensing film. In the above equation d(PdOx) and d(Au) are the modulation lengths of PdOx and Au respectively and n(Pd) and n(Au) are the refractive indexes of PdOx and Au, respectively. The second term in above equation represents the refractive index modulation with $A_i$ as modulation amplitude and the exponential term as coherent modulation contribution across whole multilayered material. Since the light transmission and absorption is dependent upon the incident light wavelength and the material distinction coefficient or imaginary part of the dielectric function, such a multilayered structure can be designed to have a balanced reflection and absorption at a specific sensing film thickness, and sublayer refractive index. For example, in the embodiment shown in FIG. 7, wherein an Au nanostructural sublayer with 1.7 nm thickness is used, the ratio of the Au sublayer to the modulation length is about 0.33. This ratio can be tuned to be sensitive to small hydrogen concentration changes, and any small variation in refractive index can be measured during absorption mechanism when there is high hydrogen concentration. Moreover, such a combination of reflectance and absorption properties can be varied with different non-hydridable materials such as Au, Ag, Ni, and Cu, for example.

In one embodiment, the multilayered sensing material has a nanostructural surface morphology to enable H ions diffusion. In another embodiment, the sensing material has a nanoporous structure with Ni as the non-hydridable layer. In yet another embodiment, the sensing material has a nanoparticle structure with Au as the non-hydridable layer. It should be noted that any other noble material such as silver or copper or nickel may also be used for the non-hydridable layer. The non-hydridable layers are used to ensure H ions interact with palladium nanoparticles. In one embodiment, the nanoparticle size ranges from 5 nm to 15 nm. In another embodiment, a pillar-like surface morphology is used for a fast hydride formation process in the sensing material. In a specific embodiment, the pillar like surface morphology is used along with a Pd layer of 1 nanometer as a capping layer to quickly dissolve hydrogen molecules to H+ ions for innerward diffusion.

Figure 8:
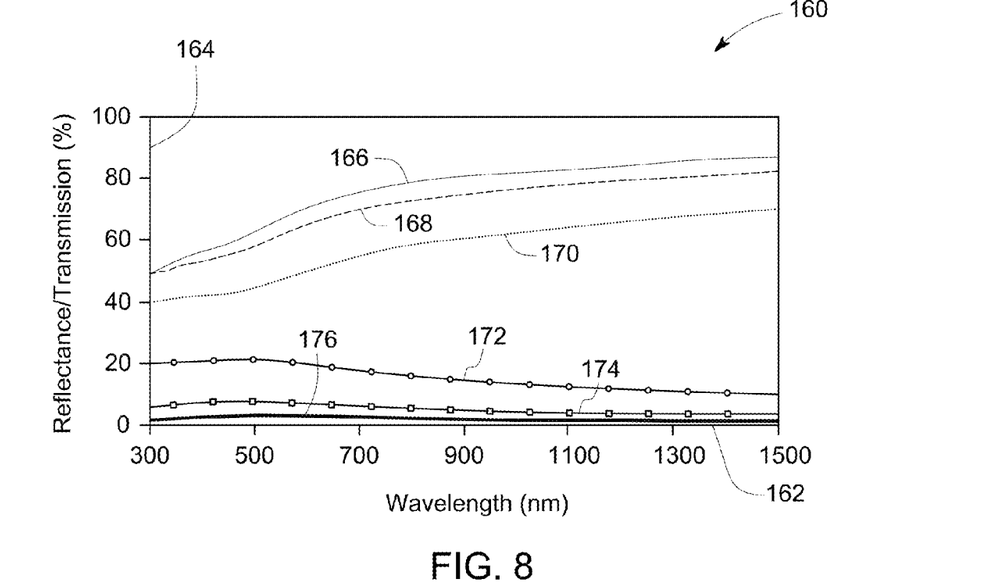
FIG. 8 is a graphical representation of simulated reflectance and transmission properties of various multilayered sensing films.

FIG. 8 depicts a plot 160 of simulated reflectance and transmission optical properties from three PdOx/Au multilayered sensing films with respect to light wavelength. The horizontal axis 162 represents the light wavelength in nanometers, and the vertical axis 164 represents reflectance and transmission properties of the film in percentage. The plot 160 shows three reflectance 166, 168, 170 and three transmission curves 172, 174 and 176 for three different PdOx/Au multilayered films. Curves 166 and 172 relate to a four-bilayer film having a thickness of 19 nm. Curves 168 and 174 relate to a seven-bilayer film with a thickness of 32.5 nm, and curves 170 and 176 relate to a ten-bilayer film having a thickness of 45 nm. It can be seen from the plot 160 that a high sensitivity region is in the wavelength range from 500 to 800 nm. In other words, the reflectance and the transmission have maximum value in the wavelength range from 500 to 800 nm. Further, both the reflectance and the transmission show clear dependence upon the light wavelength. At about 550 nm, the reflectance from the 19 nm thickness film is about 45%, while the 32.5 nm and 45 nm films have 60% to 67% reflectivity. Further, it can be seen that the transmission curves are less sensitive in the visible optical wavelength range. It can also be seen that at wavelengths greater than 500 nm, thicker films have higher reflectance and lower transmission. In one embodiment, an optimized H2 purity detection sensitivity requires a light source with its wavelength ranging from 500 nm to 800 nm, and the total thickness of the multilayered sensing material ranging from 10-40 nm, or a nominal thickness of about 25 nm.

Figure 9:
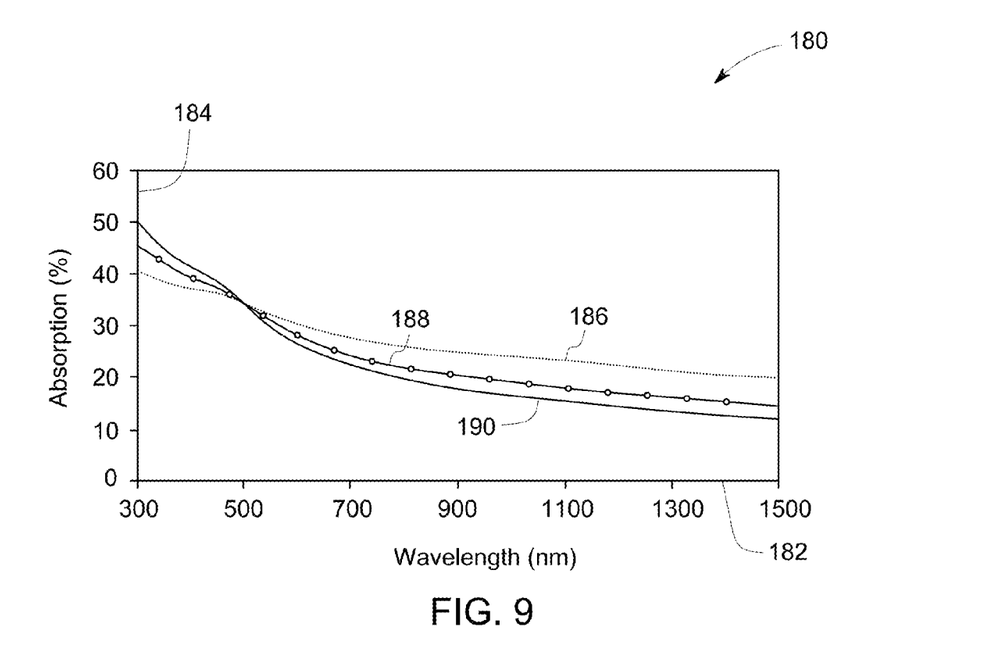
FIG. 9 is a graphical representation of simulated absorption properties of various multilayered sensing films.

FIG. 9 depicts a plot 180 of simulated optical absorption properties from the same three PdOx/Au multilayered sensing films described in FIG. 8 with respect to light wavelength. The horizontal axis 182 represents the light wavelength in nanometer, and the vertical axis 184 represents absorption properties of the film in percentage. The plot 180 shows three curves 186, 188, and 190 for the three films 19 nm, 32.5 nm, and 45 nm respectively. As can be seen from the plot, for wavelengths higher than 500 nm the thinner film has a higher absorption than the thicker films, and for wavelengths less than 500 nm the thicker film has a higher absorption compared to the thinner films. Thus, from FIGS. 8 and 9 it can be seen that, for wavelengths greater than 500 nm, a thinner film is more useful, whereas for wavelengths lower than 500 nm, a thicker film is more useful. Since the absorption is strongly dependent upon the sensing material and hydride concentration, it helps in artificially modulating H2 purity detectability by hydride formation induced reflectance and transmission. Further absorption is also dependent upon the multilayered materials or structural parameters.

Figure 10:
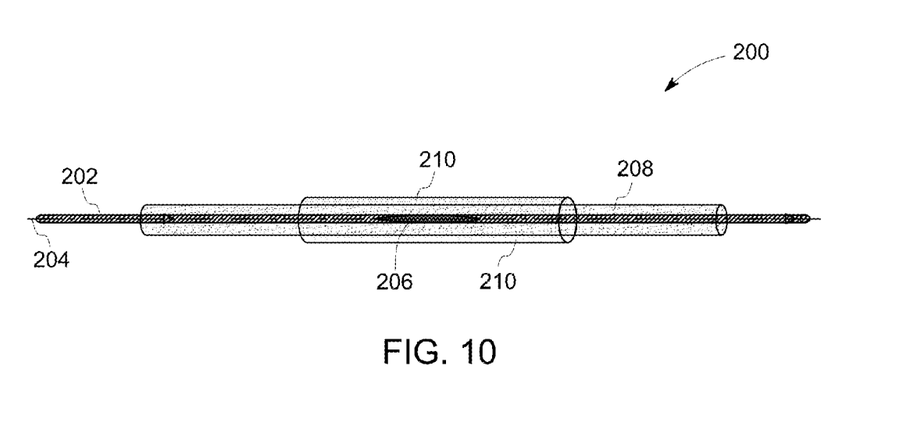
FIG. 10 is a schematic view of a sensing material and tilted and apodized fiber grating integrated fiber gas hydrogen purity sensor in accordance with an embodiment of the present invention.

FIG. 10 shows another fiber gas hydrogen purity sensor 200 according to an embodiment of the present invention. In one embodiment, the fiber gas hydrogen purity sensor 200 is an integration of the fiber grating and a sensing chip material made by a sputtering process. The fiber gas hydrogen purity sensor 200 includes a central fiber core 202 that extends along an axis 204 and includes a refractive index periodic modulated grating. In one embodiment, the central fiber core comprises GeO2 and F co-doped silica and has a diameter ranging from about 5 microns to about 9 microns. The periodic modulation may comprise an apodized, blazed, or blazed and apodized modulation, for example, for increasing guided core mode coupling to cladding modes by shedding guided mode field energy to the fiber cladding. In one embodiment, the refractive index periodic grating comprises a long-period fiber grating (LPG) structure 206 positioned surrounding the fiber core 202.

A fiber cladding 208 is circumferentially disposed about the fiber core 202 and, in one embodiment, has an outer diameter of about 125 microns made from pure silica. In one embodiment, the fiber cladding 208 is configured to act as a waveguide for light propagation through the fiber core 202. A broadband tunable light source (not shown) is positioned in light communication with the optical fiber cable and emits a near infrared light that propagates through the fiber core 202.

A nanostructural multilayered sensing layer 210 is disposed about the fiber cladding 208 of the LPG structure 206. The sensing layer 210 is configured to effectively assist the coupling of the mode of the fiber cladding 208 to the fundamental mode of the fiber core by a refractive index variation, an optical absorption change, a sensing material stress change, or a combination thereof, for example. The sensing layer 210 is sensitive and/or activated by interactions with a hydrogen gas that induces the refractive index variation, the absorption change, the sensing material stress change, or other change. In one embodiment, the multilayered nanostructural sensing film 140 is described with respect to FIG. 7. As described earlier, a hydride formation on the nanostructural multilayered sensing film 140 turns its ambient opaque mirror-like surface into a more translucent surface. The formation of the hydride changes the cladding mode boundary and coupling efficiency so that the transmission wavelength and its power loss of the fiber grating-based hydrogen purity sensor are modulated.

In a particular embodiment, the fiber gas hydrogen purity sensor 200 has a length along a longitudinal axis 204 of the optical fiber core 202 of about 10 millimeters to about 50 millimeters. The LPG structure 206 has a length along the longitudinal axis 204 of about 10 millimeters to about 30 millimeters with a cladding diameter of about 0.05 millimeter to about 0.125 millimeters. The LPG structure 206 has a modulation along the longitudinal axis 204 with a pitch size of about 100 microns to about 600 microns. The LPG structure 206 is configured to effectively shed fundamental mode energy to the modes of the fiber cladding 208 with apodized or blazed refractive index modulation profile. When the refractive index of the sensing material of the sensing layer 210 is lower than the fiber cladding 208, the modes of the fiber cladding 208 are guided by sensing material/cladding and fiber core interfaces. Partial light energy dissipates into the sensing material by an evanescent field while the cladding modes partially dissipate the energy into the sensing coating layer as radiation modes.

Figure 11:
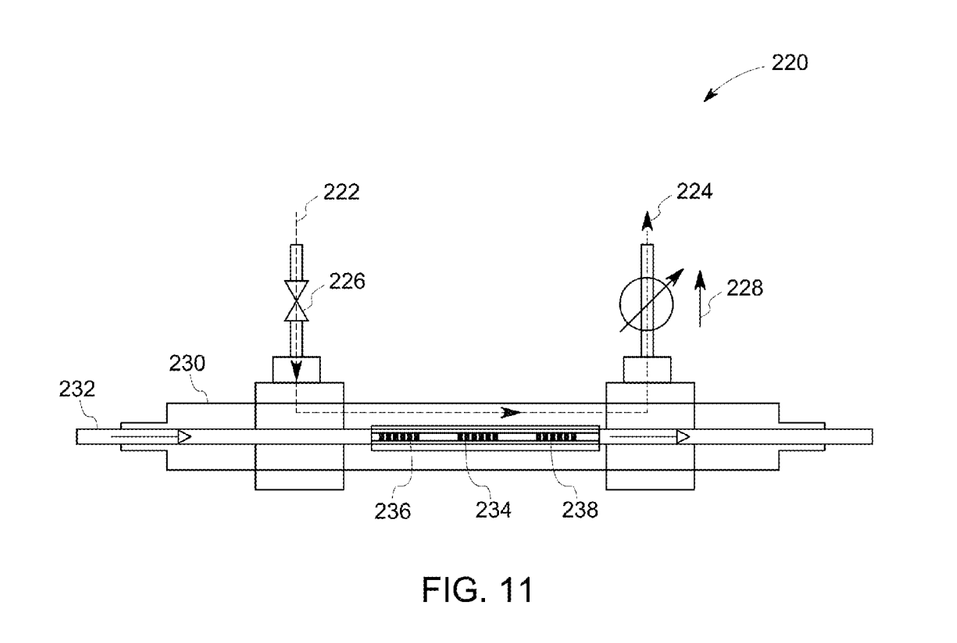
FIG. 11 is a schematic representation of a fiber grating array-based fiber gas hydrogen purity sensor package in accordance with an embodiment of the present invention.

FIG. 11 shows a fiber grating array based fiber gas hydrogen purity sensor package 220 according to an embodiment of the present invention. The fiber gas hydrogen purity sensor package 220 includes a gas inlet 222, a gas outlet 224, an inlet valve 226, and a pressure control valve 228. The inlet valve 226 controls the amount of gas injected in a quartz tube 230, and the pressure control valve 228 controls the gas pressure inside the tube 230. In one embodiment, the sampling gas or hydrogen enters the quartz tube 230 from the gas inlet 222, travels through the tube 230, and releases through the gas outlet 224. A sensing fiber 232 is installed inside the tube 230 which, in the illustrated embodiment, has three fiber sensors 234, 236 and 238. In one embodiment, a long-period fiber grating (LPG) structure and a sensing material integrated fiber gas hydrogen purity sensor (FGHPS) 234 are positioned at the center of the quartz tube package center 230. In another embodiment, two fiber Bragg grating (FBG) structures 236 (FBG1), 238 (FBG2) are installed on either side of the FGHPS 234 to measure localized temperatures for correcting gas sensor wavelength shift induced by flow-rate fluctuation at any time. The difference $\Delta\lambda(t)$ between two FBGs' wavelength ($\lambda1(t)$ and $\lambda2(t)$) shift is directly proportional to a gas flow variation or temperature fluctuation and is given by $$\Delta\lambda(t)=\lambda1(t)-\lambda2(t) \propto \text{gas flowrate, or.} \quad (2)$$

$$\Delta\lambda(t)=\lambda1(t)-\lambda2(t) \propto \text{temperature fluctuation,} \quad (3)$$

Equations (2) and (3) indicates that when the gas flowrate is kept constant, $\Delta\lambda(t)$ will reflect the local temperature fluctuations.

Since the hydrogen gas has high thermal conductivity to carry away the thermal energy from the fiber gas sensor, the use of fiber Bragg grating can directly measure wavelength shift due to thermal loss by $$\Delta\lambda1(t)=\lambda1(t1)-\lambda1(t2) \propto \text{H2 gas concentration,} \quad (4)$$

$$\Delta\lambda2(t)=\lambda2(t1)-\lambda2(t2) \propto \text{H2 gas concentration.} \quad (5)$$

At any time, both the flow rate and the hydrogen concentration are simultaneously monitored to provide accurate H2 purity detection.

Figure 12:
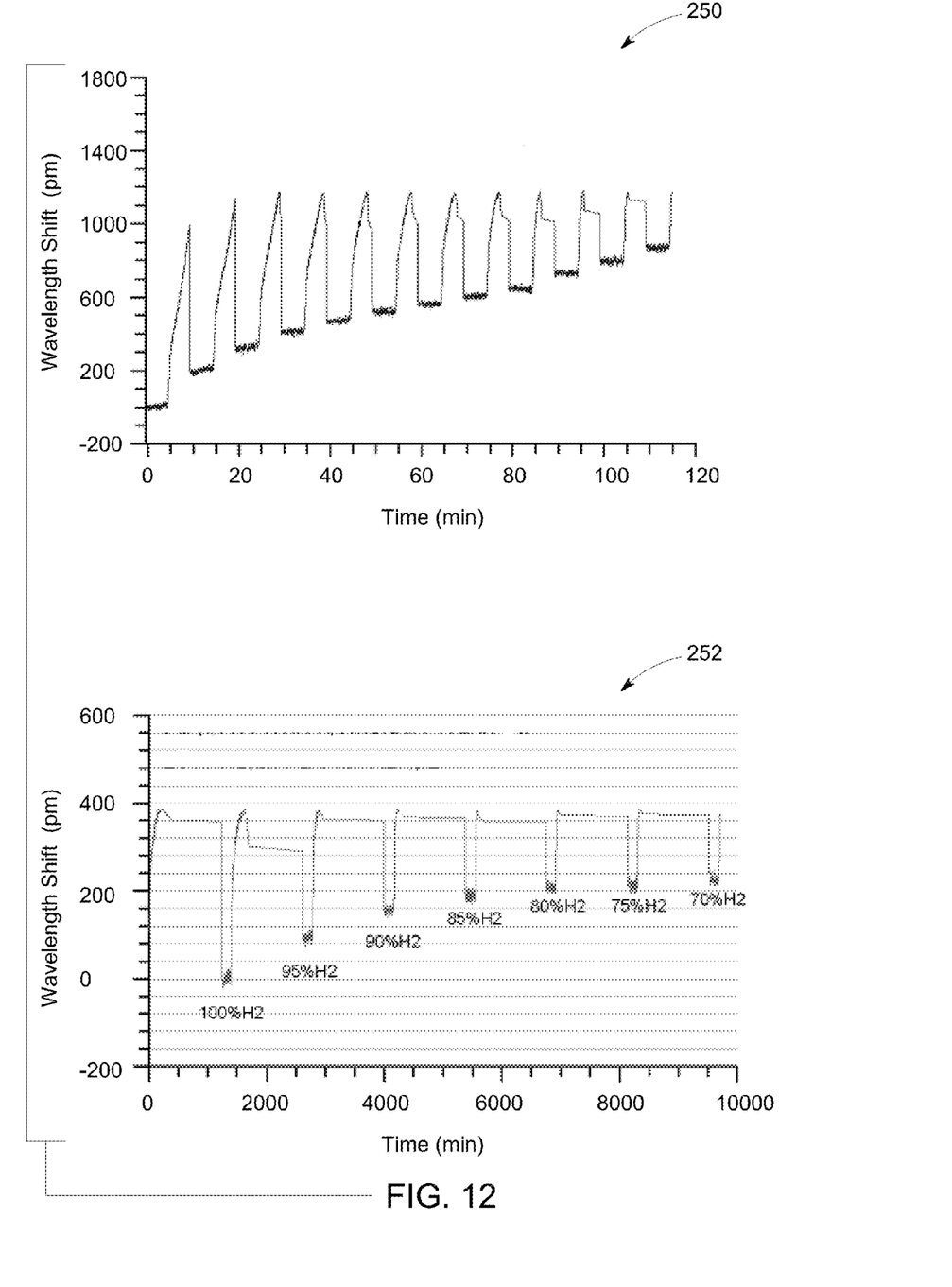
FIG. 12 is a graphical representation of a fiber gas purity sensor response in accordance with an embodiment of the present invention.

FIG. 12 shows two fiber gas purity sensor responses 250 and 252 for different hydrogen purities. The response 250 is of a fiber gas hydrogen purity sensor having 15 bilayers of 2.8 nm PdOx and 1.7 nm Au. The thickness of each bilayer is about 4.5 nm, and the total thickness is 67.5 nm for 15 bilayers or 31 multilayers. It should be noted that in order to quickly increase conversion efficiency from hydrogen molecular (H2) to hydrogen ion (H+), 1 nm thick Pd is used as a capping layer onto the multilayered sensing film. Similarly, the response 252 is of a fiber gas hydrogen purity sensor having 5 bilayers of 3 nm PdOx and 1.0 nm Au. The nominal thickness of each bilayer is about 4.0 nm, and the total thickness is 205 nm for 5 bilayers or 11 multilayers. The apparatus for which hydrogen purity is measured contained 100% H2 at first, then the H2 purity was reduced by 5% in step. For diluting hydrogen, N2 gas was introduced in the apparatus. The interaction between the sensing material and diluted H2 gas forms hydrides in the sensing material. The peak wavelength of the fiber gas sensor increases or decreases with increased N2 or decreased N2 concentration. It can be seen from the responses that both fiber sensor prototypes have sensitivity to H2 purity change. Further it can also be seen that the thicker sensing film integrated purity sensor has larger response amplitude compared to the thinner sensing film integrated purity sensor.

Figure 13:
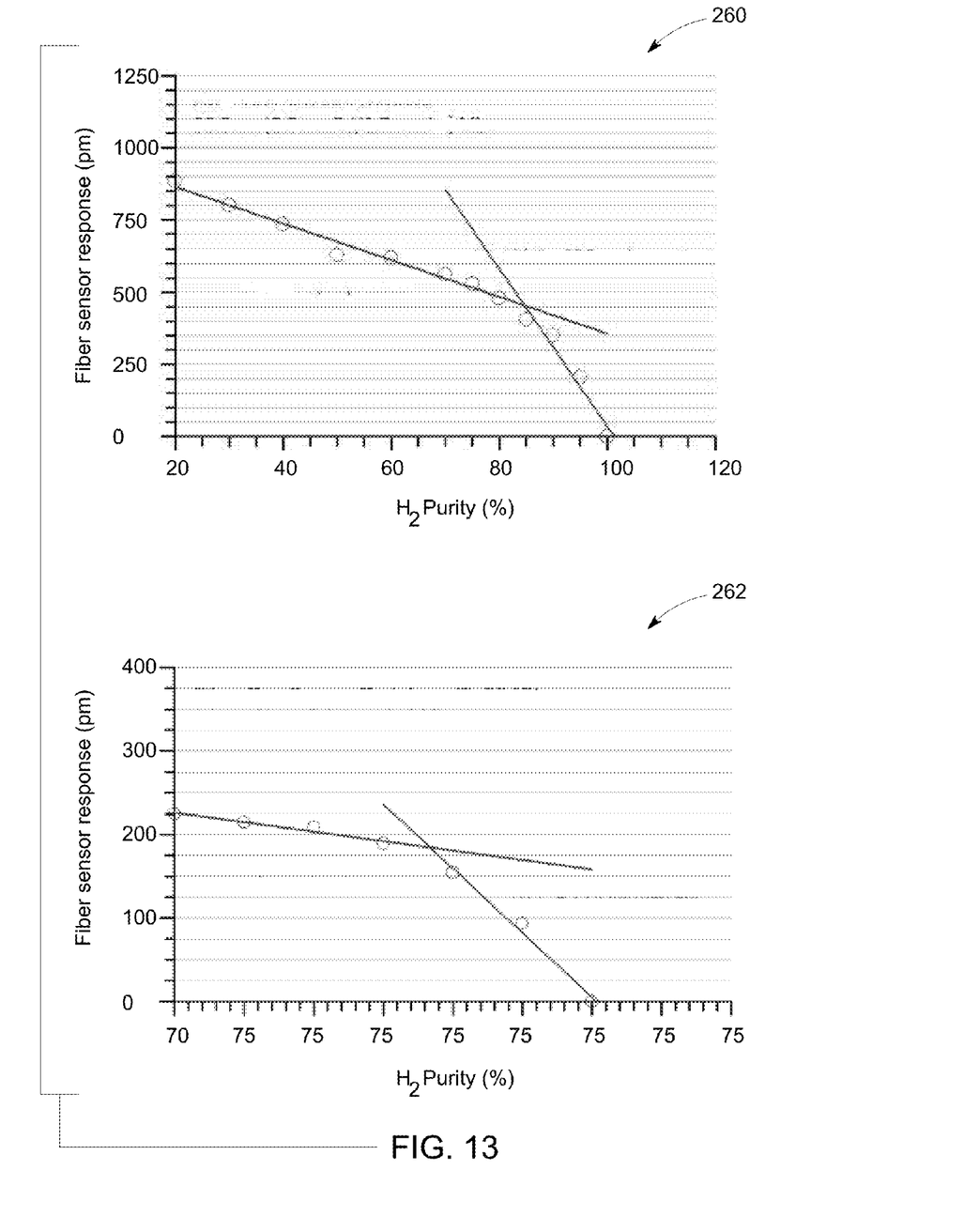
FIG. 13 is a graphical representation of sensitivity responses from fiber gas purity sensors in accordance with an embodiment of the present invention.

FIG. 13 shows sensitivity responses 260, 262 for thinner and thicker sensing material integrated fiber gas purity sensors described with respect to FIG. 12. In both responses two linear sensitivities have been identified. For the response 260, the first linear range is from low-H2 to 80% H2, for which the sensitivity is about 6.4 pm/percent for H2 concentration; while the second linear range is from 80% to 100% H2 purity with 27.3 pm/percent sensitivity. For the response 262, the first linear range is about 2.3 pm/percent sensitivity for H2 concentration from 70% to 85% or so; while second linear range is from ~85% to 100% H2 purity with 15.4 pm/percent sensitivity. Since the fiber sensor signal interrogation unit has ±5 pm accuracy, the estimated gas detection resolution is about 1% for low-H2 sensing range, and about 0.2% H2 for 80-100% H2 purity range with the thicker sensing material integrated fiber gas sensor prototype. It can also be seen that the sensitivity significantly drops with the thinner sensing material integrated fiber gas sensor prototype by a factor of ~1.5-2.5 because of high absorption at 1.5 μm, as shown in FIG. 9.

One of the advantages of the described hydrogen purity sensors is high sensitivity and accuracy when measuring high hydrogen purity. The FBG1-FGHPS-FBG2 sensing array is capable of measuring hydrogen purity in the range of 70% to 100%, have a low complexity, and can be safely deployed anywhere. Thus, safety measures for the apparatus where these sensors are installed may become less complex and less costly.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for measuring hydrogen purity comprising:
a light source for providing an optical signal through a fiber optic cable;
a hydrogen purity sensor for receiving the optical signal, the hydrogen purity sensor comprising a multilayered nanostructural film reactive to hydrogen and comprising a plurality of hydridable material layers alternating with a plurality of non-hydridable material layers;
a photodetector for receiving a reflected optical signal from the hydrogen purity sensor; and
processing circuitry coupled to the photodetector for analyzing the reflected optical signal.

2. The system of claim 1, wherein the hydridable material comprises a high refractive index material and the non-hydridable material comprises a low refractive index material.

3. The system of claim 2, wherein the high refractive index material comprises a material with higher refractive index compared to a fiber cladding of the fiber optic cable and the low refractive index material comprises a material with lower refractive index compared to the fiber cladding of the fiber optic cable.

4. The system of claim 2, wherein each hydridable layer thickness is in the range of 1 to 5 nanometers and each non-hydridable layer thickness is in the range of 1 to 3 nanometers.

5. The system of claim 4, wherein the hydridable material comprises a palladium or a palladium alloy.

6. The system of claim 5, wherein the palladium alloy comprises Pd(x)M(1−x), wherein M is a material comprising Ag, Au, Cu or Ni.

7. The system of claim 5, wherein the palladium alloy comprises PdOx.

8. The system of claim 4, wherein the non-hydridable material comprises gold, silver, nickel, copper, or a combination thereof.

9. The system of claim 1, wherein the fiber optic cable comprises a multi-furcated fiber reflectance probe.

10. The system of claim 9, further comprising a sensing probe tip house housing the multilayered nanostructural film and one end of the multi-furcated fiber reflectance probe.

11. The system of claim 10, wherein the sensing probe tip house further comprises a filter for filtering hydrogen gas entering the sensing probe tip house.

12. The system of claim 10, wherein the multi-furcated fiber reflectance probe tip and the multilayered nanostructural film are separated by a distance based on a desired amplitude of the reflected signal.

13. The system of claim 1, wherein the multilayered nanostructural film thickness is in the range of 10 to 100 nanometers and wherein the multilayered nanostructural film has maximum sensitivity in reflectance and absorption in the light source wavelength of 500-800 nm range.

14. The system of claim 1, wherein the hydridable material comprises a palladium or palladium alloy and the non-hydridable material comprises a noble metal; wherein each hydridable layer thickness is in the range of 1 to 5 nanometers and each non-hydridable layer thickness is in the range of 1 to 3 nanometers; and wherein the multilayered nanostructural film thickness is in the range of 10 to 100 nanometers.

15. A hydrogen purity sensor, comprising:
a fiber core;
a refractive index periodic modulated grating structure positioned about the fiber core;
a fiber cladding positioned surrounding the refractive index periodic modulated grating structures; and
a multilayered sensing film reactive to hydrogen and positioned about the fiber cladding comprising a modulated structure comprising a plurality of hydridable material layers alternating with a plurality of non-hydridable material layers.

16. The hydrogen purity sensor of claim 15, wherein the hydridable material comprises a high refractive index material and the non-hydridable material comprises a low refractive index material.

17. The hydrogen purity sensor of claim 16, wherein the hydridable material comprises palladium or palladium alloy with high refractive index and the non-hydridable material comprises noble metal with low refractive index.

18. The hydrogen purity sensor of claim 17, wherein the noble metal comprises at least one of a gold, silver, nickel or copper.

19. The hydrogen purity sensor of claim 15, wherein the refractive index periodic modulated grating structure comprises a long-period fiber grating structure.

20. The hydrogen purity sensor of claim 19 further comprising two fiber Bragg grating structures disposed on either side of the long-period fiber grating structure for simultaneously measuring localized temperature variations due to sensor wavelength shift introduced by flow rate and gas thermal conductivity variation.

21. The hydrogen purity sensor of claim 15, wherein the refractive index periodic modulated grating structure comprises one of a blazed profile, an apodized profile, or a blazed and apodized profile.

22. The hydrogen purity sensor of claim 15, wherein the multilayered sensing film comprises at least one of a nanoporous structure, and a nanoparticle structure.

23. The hydrogen purity sensor of claim 15, wherein the multilayered sensing film comprises a pillar-like surface morphology.

* * * * *